US007078179B2

(12) United States Patent
Di Colandrea et al.

(10) Patent No.: US 7,078,179 B2
(45) Date of Patent: Jul. 18, 2006

(54) SELECTABLE GENE MARKER SYSTEM BASED ON EXPRESSION OF N-ACETYLLACTOSAMINIDE 3-α GALACTOSYLTRANSFERASE

(75) Inventors: Teresa Di Colandrea, Ames, IA (US); Cherisa Meyer, Ames, IA (US); Won-Bin Young, Ames, IA (US); James N. Higginbotham, Hendersonville, TN (US); Mario Mautino, Ames, IA (US); Charles J. Link, Jr., Ames, IA (US)

(73) Assignee: Newlink Genetics Corporation, Ames, IA (US)

( * ) Notice: Subject to any disclaimer, the term of this patent is extended or adjusted under 35 U.S.C. 154(b) by 29 days.

(21) Appl. No.: 10/838,750

(22) Filed: May 4, 2004

(65) Prior Publication Data

US 2005/0250107 A1 Nov. 10, 2005

(51) Int. Cl.
*G01N 33/567* (2006.01)
*G01N 33/53* (2006.01)
*C12Q 1/68* (2006.01)
*C12N 15/63* (2006.01)
*C12N 15/86* (2006.01)

(52) U.S. Cl. ............... 435/7.21; 435/6; 435/7.1; 435/455; 435/456

(58) Field of Classification Search ............... None
See application file for complete search history.

(56) References Cited

U.S. PATENT DOCUMENTS

2001/0034028 A1* 10/2001 Link et al. ............... 435/6

OTHER PUBLICATIONS

Bouhours J-F, Richard C, Ruvoen N, Barreau N, Naulet J, Bouhours D, Characterization of a polyclonal anti-Galα1-3Gal antibody from chicken, 1998, Glycoconjugate Journal 15:93-99.*
Zurcher AW, Lang AB, Aebischer I, Miescher S, Stadler BM, IgE-producing hybridomas establihed after B-cell culture in the CD40 system, 1995, Immunology Letters 46:49-57.*
Lehmann J, Huehn J, de la Rosa M, Maszyna F, Kretschmer U, Krenn V, Brunner M, Scheffold A, Hamann A, Expression of the integren aeb7 identifies unique subsets of CD25+ as well as CD25- regulatory T cells, 2002, Proc Natl Acad Sci USA 99:13031-13036.*

Galili U et al., "Preparation of autologous leukemia and lymphoma vaccines expressing alpha-gal epitopes", Journal of Hematotherapy and Stem Cell Research. U.S. Aug. 2001; 10(4):501-511 Aug. 2001.
La Temple D.C. et al., "Synthesis of E-Galactosyl Epitopes by Recombinant E1,3Galactosyltransferase for Opsonization of Human Tumor Cell Vaccines by Anti-Galactose", Cancer Research, American Association for Cancer Research, Baltimore, Md, US, 56:3069-3074; Jul. 1996.
La Temple, Denise C. et al., "Increased immunogenicity of tumor vaccines complexed with anti-gal: Studies in knockout mice for E1, 3galactosyltransferase", Cancer Research, American Association for Cancer Research, Baltimore, MD, US, 59(4):3417-3423; Jul. 1999.
Gorelik E., et al., "Alterations of cell surface carbohydrates and inhibition of metastatic property of murine melanomas by E1,3 galactosyltransferase gene transfection", Cancer Research, American Association for Cancer Research, Baltimore, Md, US, 55(18):4168-4173; Sep. 1995.
Galili Uri et al., "Expression of E-gal epitopes on ovarian carcinoma membranes to be used as a novel autologous tumor vaccine", Gynecologic Onocology, 90(1):100-108; Jul. 2003.
Yoshimura N. et al., "Expression of xenoantigen transformed human cancer cells to be susceptible to antibody-mediated cell killing", Cancer Letters. Ireland 164(2):155-160; Mar. 2001.

* cited by examiner

*Primary Examiner*—Dave Trong Nguyen
*Assistant Examiner*—Patrick S. Riggins
(74) *Attorney, Agent, or Firm*—McKee, Voorhies & Sease, P.L.C.

(57) ABSTRACT

A method is described for the rapid identification and isolation of cells based on the presence or absence of an ectopically-expressed N-acetyllactosaminide 3-α Galactosyltransferase (αGT) enzyme for the production of αGalactosyl-(1,3)Galactosyl (αGal) epitopes on the surface of αGal-negative cells. These cells which are genetically modified to express the αGT enzyme and αGal epitopes on glycosylated lipids and proteins of the cell surface are then labeled via an antibody composition which recognizes and binds the αGal epitopes on the cell surface. Cells labeled with the anti-αGal antibody can be isolated by sorting via fluorescence activated cell sorting (FACS), or by magnetic panning techniques. This method is suitable for the rapid positive or negative selection of αGal-positive cells from within a population of αGal-negative cells without the need to expose cells to antibiotics for any period of time. In addition, the specification provides a method for the production and purification of anti-αGal antibodies from chicken egg yolk.

34 Claims, 7 Drawing Sheets nucleotide sequence of *Mus musculus* ΔGT

```
0001 cgtcttagga ggctggagat tctgggtgga gccctagccc tgccttttct tagctggctg
0061 acaccttccc ttgtagactc ttcttggaat gagaagtacc gattctgctg aagacctcgc
0121 gctctcaggc tctgggagtt ggaaccctgt accttccttt cctctgctga gccctgcctc
0181 cttcggcagg ccagagctcg acagaagctc ggttgctttg ctgtttgctt tggagggaac
0241 acagctgacg atgaggctga ctttgaactc aagagatctg cttacccag tctcctggaa
0301 ttaaaggcct gtactacctt gctggacct aagattttca tgatcactat gcttcaagat
0361 ctccatgtca acaagatctc catgtcaaga tccaagtcag aaacaagtct tccatcctca
0421 agatctggat cacaggagaa aataatgaat gtcaagggaa aagtaatcct gttgatgctg
0481 attgtctcaa ccgtggttgt cgtgttttgg gaatatgtca acagcccaga cggctctttc
0541 ttgtggatat atcacacaaa aattccagag gttggtgaga acagatggca gaaggactgg
0601 tggttcccaa gctggtttaa aaatgggacc cacagttatc aagaagacaa cgtagaagga
0661 cggagagaaa agggtagaaa tggagatcgc attgaagagc ctcagctatg ggactggttc
0721 aatccaaaga accgcccgga tgttttgaca gtgaccccgt ggaaggcgcc gattgtgtgg
0781 gaaggcactt atgcacagc tctgctggaa aagtactacg ccacacagaa actcactgtg
0841 gggctgacag tgtttgctgt gggaaagtac attgagcatt acttagaaga ctttctggag
0901 tctgctgaca tgtacttcat ggttggccat cgggtcatat tttacgtcat gatagatgac
0961 acctcccgga tgcctgtcgt gcacctgaac cctctacatt ccttacaagt ctttgagatc
1021 aggtctgaga agaggtggca ggatatcagc atgatgcgca tgaagaccat tggggagcac
1081 atcctggccc acatccagca cgaggtcgac ttcctcttct gcatggacgt ggatcaagtc
1141 tttcaagaca acttcggggt ggaaactctg gccagctgg tagcacagct ccaggcctgg
1201 tggtacaagg ccagtcccga gaagttcacc tatgagaggc gggaactgtc ggccgcgtac
1261 attccattcg gagaggggga ttttactac cacgcggcca tttttggagg aacgcctact
1321 cacattctca acctcaccag ggagtgcttt aaggggatcc tccaggacaa gaaacatgac
1381 atagaagccc agtggcatga tgagagccac ctcaacaaat acttcctttt caacaaaccc
1441 actaaaatcc tatctccaga gtattgctgg gactatcaga taggcctgcc ttcagatatt
1501 aaaagtgtca aggtagcttg gcagacaaaa gagtataatt tggttagaaa taatgtctga
1561 cttcaaattg tgatggaaac ttgacactat tactctggct aattcctcaa acaagtagca
1621 acacttgatt tcaactttta aagaaacaa tcaaaaccaa acccactac catggcaaac
1681 agatgatttc tcctgacacc ttgagcctgt aatatgtgag aaagagtcta tgcaagtaa
1741 tcaggtataa attctcaatg atttcttata tattctgggt cttgggaaaa cttgattcta
1801 gaaatcaaaa ttaatttgac aaggaaaag cagatgccgg aaacttcttc ccagtctgtc
1861 atacaattca ccactggcca ggtgctgaga gaagcattag ggaacagtgt gggttgtgtc
1921 agagttggac ggctccatcc ctttggcttc attatcttcc tcctcatgga gattctaaag
1981 caacccagag aggctttgca gccagagacc tttaataagg atgccaatgt gaccatcagt
2041 ctgtaaaagc tgatggctcc aggagcgctg gcagtccagg ccccactagg ctattgtttc
2101 tgtcctgggc ataaaggagg cagagatgc caatagctac tttggtggca catgttcaga
2161 gtccaggaaa aatcaagggt gaccacttag agggacatag gacttggggt tggtgattga
2221 actgagttac aaacacagac agcttttcttc aggatgacta acagcaggaa ttgaatggaa
2281 agtgtgttca ttttgttttg cccaaattgt attcatgctg ttagctttgt gtgttgagcc
2341 ctgtggagag ggtgtgactg tatcagggaa ggagagtacc tcagcggact gaggaccagc
2401 accctattat atcagaagac aatctctcat catcaggtcc tacctacaac ctgctctgaa
2461 cctccgagtt cctcagccca tcgtgttcca gtgtggggc ctgtatggag caggtgactg
2521 aagacaaagc cccctgtcac atgacctcat ttcccctgct ctagtactat gcaagtgtga
2581 cagccagcca gccagatgta ctggacaaca taggaaccga ctttatggca atgggagccg
2641 cagtcactac aacggagctg ctgaaggttc tgttccccgc tctgagagcc tgcaggagcc
2701 cctgtatagg tggttctcaa cctatgggtc gcgacccctt gggaagtgt taaatgaccc
2761 tttcacaggt gtcccctaag acggttaaaa aacatagata tttccactct gactggtaac
2821 agtagcagaa ttacagttat gaaatagcaa gggaaataat tctggggttc gtgtcatcca
2881 taccatgagg agctacatta ggtcacatca ttagggaagt tgagaagcat agctctactt
2941 gggtatttaa gcaaattatg caaagggggt tgtcgctctg tgttctgtgt atgcatatat
3001 ttatattttg cttgtcttcc agtttaggtc aatctgtttc ttcctttaag cagtttattt
3061 aaaaggccat tgcaccatct tggtgaacag catgagggt ttcaataaaa aataggatct
3121 tacctttgtc cacagggctc tacctcttac ttttcaattg tgaacaaaa aggtcgcaca
3181 cccagaggca acaaaaccca cagaattcct gaaccaatgg gagatgccaa tggaagcaga
3241 gcttgcacat ctgctaaaaa ttctgcctct ctgtcactgt gctggatccg tctaaagtgg
3301 gacagttcaa tggtctgaaa gtttcaaaaa ggctggggaa tttgagggga ttttttttta
3361 aaataaaatt gatccaagtt taaatctcta atgagtaagc ttaggatttt attaaaggta
3421 attttagac attcttcaaa ataagaattc (SEQ ID NO:1)
```

Fig 2 amino acid sequence of *Mus musculus* ΔGT

```
  1 MNVKGKVILL MLIVSTVVVV FWEYVNSPDG SFLWIYHTKI PEVGENRWQK DWWFPSWFKN
 61 GTHSYQEDNV EGRREKGRNG DRIEEPQLWD WFNPKNRPDV LTVTPWKAPI VWEGTYDTAL
121 LEKYYATQKL TVGLTVFAVG KYIEHYLEDF LESADMYFMV GHRVIFYVMI DDTSRMPVVH
181 LNPLHSLQVF EIRSEKRWQD ISMMRMKTIG EHILAHIQHE VDFLFCMDVD QVFQDNFGVE
241 TLGQLVAQLQ AWWYKASPEK FTYERRELSA AYIPFGEGDF YYHAAIFGGT PTHILNLTRE
301 CFKGILQDKK HDIEAQWHDE SHLNKYFLFN KPTKILSPEY CWDYQIGLPS DIKSVKVAWQ
361 TKEYNLVRNN V   (SEQ ID NO:2)
```

Fig 3

SELECTABLE GENE MARKER SYSTEM BASED ON EXPRESSION OF N-ACETYLLACTOSAMINIDE 3-α GALACTOSYLTRANSFERASE

FIELD OF INVENTION

The present invention relates generally to the fields of cellular and molecular biology, functional genomics, gene transfer and immunology, and more particularly to the isolation, identification and separation of cells which have been engineered to express heterologous nucleotide sequences from a population of cells.

BACKGROUND OF THE INVENTION

Functional genomics often requires the construction of gene delivery systems to force the expression of recombinant cDNA sequences in live cells. The resulting specific protein product can then be studied for its cellular localization and influence on cellular function, differentiation and proliferation, as well as a host of phenotypic changes. The state of the art is such that any cDNA sequence of interest can be delivered to the cell and become transiently or permanently part of the cellular genome by the use of modified animal viruses. Murine retroviral vectors have emerged in the past several years as the most common vehicle to deliver marker genes. Other viral vectors such as lentiviruses, adenoviruses, herpes viruses, adeno-associated viruses, and non-viral methods such as plasmids have also been used for gene transfer.

The efficiency of gene delivery systems varies according to the gene delivery vector and the target cell type to which the genes are transferred. Thus, the recombinant DNA molecule used in gene delivery systems requires the incorporation of additional polynucleotide sequences which mediate the expression of a second protein product, which confers different phenotypic properties to genetically modified cells. These altered phenotypic characters allow for positive or negative selection of cells in different kinds of assays. In a positive selection assay, this genetic marker is used to confirm the successful introduction of the recombinant DNA molecule into the cell, and is also important in the isolation of an exclusive population of cells which expresses the recombinant DNA molecule of interest. All cells that do not express the marker are excluded from the population of interest. This allows for an accurate study of the effects of primary cDNA sequence on cellular function and phenotype.

The marker usually encodes enzymes that confer antibiotic resistance, or enzymes that complement a metabolic deficiency, fluorescent proteins, or surface markers that can be selected using appropriate ligands. Gene transfer systems also include markers such as β-galactosidase, luciferase, and alkaline phosphatase. Detection of these markers involves either cell fixation that kills the cells and the addition of a substrate. These methods are often time consuming and are prone to endogenous high background. Another group of gene transfer markers convey drug resistance and thus allow positive selection of transfected cells through selection of resistant colonies. Although drug selectable markers allow the detection of living cells by expressing the transgene that encodes an enzyme that modifies the antibiotic molecule, they require that the cells survive in a toxic environment over a long period of time. The consequences of selection methods which use antibiotics include issues of toxicity and effects on normal gene expression profiles which, in turn, can affect the interpretation of phenotypic changes associated with the introduction of recombinant DNA molecules. In addition, long selection periods associated with antibiotics can severely limit the window of time available to researchers for functional genomic analysis or cell biological observations regarding genes of interest where cells senesce takes place in culture within a short period of time. For example, the neomycin-resistance gene, which confers resistance to the neomycin analog G418, has been shown to have deleterious effects upon the expression of other genes in retroviral vectors. (Emerman, M., et al. (1986) Nucleic Acids Res. 14, 9381–9396).

More recent advances in gene delivery systems utilize a sortable marker encoded by recombinant cDNA sequences to result in a protein product that is capable of fluorescence within the cell (GFP, for example). These systems have the advantage over selection markers in that isolation of a cell population of interest can often be more rapid than with antibiotics. The disadvantage of these fluorescent, sortable markers is that they can suffer from lack of sensitivity. Furthermore, in certain cells, the level of internal auto fluorescence from a cell can overlap and interfere with the true fluorescent signal of the marker, thus preventing the efficient isolation of cells that have been modified by the delivery of recombinant DNA molecules.

Other types of selectable markers that allow for cell sorting of transduced or transfected cells are proteins that introduce epitopes on the extracellular side of the cell membrane. These membrane proteins are detected with specific ligands or antibodies that bind to extracellular domains of these proteins. This allows for fluorescence activated cell sorting if the antibody or ligand are directly or indirectly labeled with fluorescent molecules, or for magnetic sorting if the antibody or ligand are directly or indirectly linked to ferromagnetic beads. This strategy has the advantage of being highly flexible as it allows different cell sorting methods and analysis of transduced cells, but suffers from the disadvantage that it is not be very sensitive. Also, expression of transmembrane proteins might alter the phenotypic characteristics of the cell under analysis.

Controlling the expression of the introduced recombinant DNA molecule such that it can be limited to a phenotypically-distinct subset of cells within a larger general population provides additional advantages to the live isolation of specific cell types where presently no or few adequate cell-surface markers exist. Epithelial adult stem cells provide one example where few, if any, adequate cell surface markers allow for the isolation of the stem cell population in most epithelial organs upon disaggregation of the epithelial tissue. However, there exist a number of cytoplasmic and nuclear proteins which do readily mark the epithelial stem cell population within an epithelial tissue. Thus, the introduction of a phenotypic-specific selectable marker to drive the expression of cell surface epitopes would allow for the isolation of a distinct subpopulation of modified cells that adhered to the phenotype of an adult stem cell of a given epithelial organ. Similarly, there are also few identified unique cell surface markers to adequately separate tumor cells from normal epithelia within an epithelial tissue. This inability to actively sort phenotypically distinct cells hampers clinical and diagnostic research efforts in cancer biology. Correctly identifying and isolating the slow growing tumor cell population from the rest of the epithelial tissue could therefore yield greater progress in identifying those genes which are truly altered in mechanisms of cancer. Thus, the invention of an innocuous marker with no discernable toxicity that is strongly detectable and can enable the rapid isolation of a population of marked cells would offer great advantages to the fields of finctional genomics and cell biology.

It is therefore a primary objective of the present invention to provide a gene transfer marker that overcomes the deficiencies of currently available gene transfer markers as described above.

It is another objective of the present invention to provide a gene transfer marker that provides rapid and sensitive identification of gene transfer in living mammalian cells.

These and other objectives will become apparent from the following description.

BRIEF SUMMARY OF THE INVENTION

The invention allows for the live isolation or visualization of a specific population of cells subjected to gene transfer that contain a polynucleotide of interest, from a larger population of cells using a novel, innocuous, selectable marker. The use of this marker to capture cells has the advantage of being a rapid selection method without the requirement of antibiotics. Thus, the invention comprises, methods, vectors, transformed cells, expression constructs, using a novel marker for viral and non-viral expression vectors for the generation of transgenic cell lines for any desired application.

According to the invention the αGal epitope is used as a cell surface selection marker and vectors for the introduction of heterologous nucleotide sequences into cells are engineered to include an expression construct for the expression of a protein such as αGT to facilitate the expression of an αGal epitope. Upon expression in transformed cells the αGT catalyzes the production of an αGal epitope on the surface of said cells. This epitope thus becomes a phenotypic difference between cells that contain the vectors and those that do not and may be exploited by any of a number of different protocols to isolate or visualize transformed cells in within a population of cells. Cells that can be selected and rapidly isolated using this method are any αGal negative cells (cells which do not express a functional αGal epitope including but not limited to all human cells, old world primate cells, insect cells, avian cells, and in mammalian cells where the αGT locus has been disrupted.

Polynucleotide sequences encoding αGT are known and readily available to those of skill in the art through the papers referenced herein and through sources such as Genbank. Any polynucleotide sequence which encodes upon expression an αGT protein which can then mediate the expression of an αGal epitope on the cell surface may be used according to the invention. Further this αGT polynucleotide sequence can be introduced into cells of interest using any mammalian expression vector including but not limited to expression vectors constructed from adenoviruses, lentiviruses, animal retroviruses, herpes simplex viruses, human papilloma viruses, and bacterial genomes such as is the case with mammalian expression plasmids.

According to the invention the αGT encoding polynucleotide is included within a an expression construct which will include regulatory sequences operably linked thereto for the expression of the selection polynucleotide within a cell that is transformed. This can include promoter, enhancer and termination sequences. Promoter sequences can include any functional promoter in the recipient cell. This can include inducible, (that allow the promoter to respond to the addition of drugs or other activating/inhibitory agents in the culture media) tissue specific, constitutive, or developmentally specific. The regulatory elements may be specific to the selection polynucleotide within a separate expression construct, or located in tandem with the polynucleotide sequence of interest with shared regulatory elements operably linked to both polynucleotide sequences.

In yet another embodiment, the present invention can be modified to allow the transient production of αGal epitopes on the cell surface by the introduction of a mammalian expression vector that would contain loxP recombination sequences to allow for the subsequent removal of the integrated vector from the cellular genome. This would facilitate functional studies in cells where the removal of the αGT cDNA would be desired.

Once this phenotypic difference is present, any of a number of methods may be used to visualize or isolate the cells containing heterologous nucleotide sequences. The expression of this marker can be detected by binding with a specific anti-αGal antibody or by the binding of a lectin from *Griffonia simplicifolia* B4 (IB4, Link, C. J., et al., Anticancer Research. 1998, 18: 2301–2308). These molecules can be directly or indirectly conjugated to fluorophores or magnetic particles to mediate staining, or separation of the cells expressing this selectable marker by FACS or magnetic panning techniques.

In a preferred embodiment, cells that have been genetically modified to express the αGT selectable marker and express αGal epitopes in their cell surface are labeled with an anti-αGal antibody and can be subsequently isolated rapidly by sorting the labeled cells by direct or indirect staining via fluorescence activated cell sorting (FACS), or by magnetic panning techniques. The presence of the epitope on the cell surface can be further enhanced by the application of an indirect detection protocol that allows for the amplification of the marker signal and increases marker sensitivity.

DEFINITIONS

Various terms relating to the compositions and methods of the present invention are used herein above and also throughout the specification and claims.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

The term "αGT" or "N-acetyllactosaminide 3-αGalactosyltransferase" or "α-(1, 3) Galactosyl Transferase encoding sequence" or "αGT encoding sequence" means any polynucleotide sequence which encodes a protein that forms αGal epitopes by the following reaction:

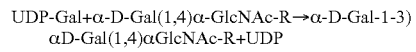
UDP-Gal+α-D-Gal(1,4)α-GlcNAc-R→α-D-Gal-1-3) αD-Gal(1,4)αGlcNAc-R+UDP

The enzyme catalog number for this enzyme is EC 2.4.1.87. Its official name is N-acetyllactosaminide 3-α-galactosyltransferase, and has numerous alternative names, such as: N-acetyllactosaminide α-1,3-galactosyltransferase; Galactosyltransferase; α-galactosyltransferase; UDP-Gal: α-D-Gal(1,4)-D-GlcNAc α-(1,3)-galactosyltransferase; UDP-Gal: N-acetyllactosaminide α-(1,3)-galactosyltransferase; UDP-Gal:N-acetyllactosaminide α-1,3-D-galactosyltransferase; UDP-Gal:-α-1->4GlcNAc-R α-1->3-galactosyltransferase; UDP-galactose-acetyllactosamine α-D-galactosyltransferase; UDP galactose: α-D-galactosyl-α-1,4-N-acetyl-D-glucosaminyl; glycopeptide α-1,3-D-galactosyltransferase; Glucosaminylglycopeptide α-1,3-galactosyltransferase; Uridine diphosphogalactose-acetyllactosamine α-1->3-galactosyltransferase; Uridine diphosphogalactose-acetyllactosamine galactosyltransferase; Uridine diphosphogalactose-galactosylacetylglucosaminylgalactosyl-glucosylceramide galactosyltransferase and α-D-galactosyl-N-acetylglucosaminylglycopeptide α-1,3-galactosyltransferase. This can include conservatively modified variants, modifications, truncations and the like as well as murine sequences, bovine or sequences from any other source known to those of skill in the art and available in Genbank, other publications or databases which retain the function of the aforementioned reaction. Typically such sequences will be at least 80% homologous or greater to the mouse or bovine αGT sequences disclosed herein.

By "αGal epitopes" is meant the trisaccharide α-D-galactosyl(1,3)-β-D-galactosyl-(1,4)-β-N-acetylglucosaminy bound to lipids or proteins through N- or O-glycosyl bonds.

By "amplified" is meant the construction of multiple copies of a nucleic acid sequences or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "animal" as used herein should be construed to include all anti-αGal synthesizing animals including those which are not yet known to synthesize anti-αGal. For example, some animals such as those of the avian species are known not to synthesize αGal epitopes. Due to the unique reciprocal relationship among animals which synthesize either anti-αGal or αGal epitopes, it is believed that many animals heretofore untested in which αGal epitopes are absent may prove to be anti-αGal synthesizing animals. The invention also encompasses cells from these animals.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (epitope or antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "anti-αGal" includes any type or subtype of immunoglobulin recognizing the αGal epitope, such as IgG, IgA, IgE, IgM or IgY anti-αGal antibody.

As used herein, the term "antigen" is meant any biological molecule (proteins, peptides, lipids, glycans, glycoproteins, glycolipids, etc) that is capable of eliciting an immune response against itself or portions thereof, including but not limited to, tumor associated antigens and viral, bacterial, parasitic and fungal antigens.

As used herein, the term "antigen presentation" is meant the biological mechanism by which macrophages, dendritic cells, B cells and other types of antigen presenting cells process internal or external antigens into subfragments of those molecules and present them complexed with class I or class II major histocompatibility complex or CD1 molecules on the surface of the cell. This process leads to growth stimulation of other types of cells of the immune system (such as CD4+, CD8+, B and NK cells), which are able to specifically recognize those complexes and mediate an immune response against those antigens or cells displaying those antigens.

A "clone" is a population of cells derived from a single cell or common ancestor by mitosis. A "cell line" is a clone of a primary cell that is capable of stable growth in vitro for many generations.

A "coding sequence" or "coding region" refers to a nucleic acid molecule having sequence information necessary to produce a gene product, when the sequence is expressed.

The term "conservatively modified variants" applies to both amino acid and nucleic acid sequences and is intended to be included whenever a reference to a specific sequence is made. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

We define the "percentage of sequence identity" of two amino acid sequences as the number of identical amino acids shared by these two amino acid sequences after a pairwise alignment divided by the total length of the shortest sequence of the pair.

We define the "percentage of sequence similarity" of two amino acid sequences as the number of identical amino acids plus conservative amino acid substitutions shared by these two sequences after a pairwise alignment, divided by the total length of the shortest sequence of the pair.

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to proteins or peptides, the term "isolated protein (or antibody)" or "isolated and purified protein (or antibody)" is sometimes used herein. This term may refer to a protein that has been sufficiently separated from other proteins with which it would naturally be associated, so as to exist in "substantially pure" form. Alternatively, this term may refer to a protein produced by expression of an isolated nucleic acid molecule.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be eukaryotic cells such as insect, amphibian, avian or mammalian cells.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected DNA or mRNA).

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleic acid construct" or "DNA construct" or "expression construct" is sometimes used to refer to a coding sequence or sequences operably linked to appropriate regulatory sequences and inserted into a vector for transforming a cell. Such a nucleic acid construct may contain a coding sequence for a gene product of interest, along with a selectable marker gene and/or a reporter gene.

The term "opsonization" of an antigen or a tumor cell is meant binding of the αGal epitopes present in the antigen or on the surface of a cell by anti-αGal antibodies, thereby facilitating detection with anti-anti-αGal antibodies or facilitating complement-binding for negative selection techniques that involve obtaining αGT negative cells from a population of αGT positive cells.

As used herein, "polynucleotide" includes reference to a deoxyribonucleotide, ribonucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNA or RNA with backbone modified for stability or for other reasons is a "polynucleotide" as that term is intended herein.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, this protein is specifically reactive to antibodies elicited to the same protein but consisting entirely of naturally occurring amino acids. The terms "polypeptide", "peptide" and "protein" are also inclusive of modifications including, but not limited to, phosphorylation, glycosylation, lipid attachment, sulfation, gamma-carboxylation of glutamic acid residues, hydroxylation and ADP-ribosylation.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g. spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. It typically consists of a heterologous promoter driving the expression of the gene of interest or of the selectable marker. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

As used herein, "selectable marker" or "sortable marker" includes reference to a polynucleotide sequence that confers upon expression a unique phenotypic character that the original cell did not have, and which allows detection and/or isolation of the cell expressing such marker.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The term "operably linked" or "operably inserted" means that the regulatory sequences necessary for expression of the coding sequence are placed in a nucleic acid molecule in the appropriate positions relative to the coding sequence so as to enable expression of the coding sequence upon binding of the necessary transcription factors. This same definition is sometimes applied to the arrangement other transcription control elements (e.g., enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The term "tumor cell" is meant a cell that is a component of a tumor in an animal, or a cell which is determined to be destined to become a component of a tumor, i.e., a cell which is a component of a precancerous lesion in an animal. Included within this definition are malignant cells of the hematopoietic system which do not form solid tumors such as leukemias, lymphomas and myelomas.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "vector" is a replicon, such as plasmid, phage, cosmid, or virus to which another nucleic acid segment may be operably inserted so as to bring about the replication or expression of the segment.

The term "reporter gene" refers to a gene that encodes a product which is easily detectable by standard methods, either directly or indirectly.

BRIEF DESCRIPTION OF THE DRAWINGS

FIG. 1A shows schematics of the method used for the separation of αGal+ cells that have been transduced with a vector expressing a gene of interest and the αGT selectable marker. Upon transduction, expression of αGT will direct the synthesis of surface αGal epitopes. These epitopes can be labeled with anti-αGal IgY antibodies. These antibodies can be conjugated to biotin in which case anti-biotin antibodies or streptavidin can be used for the second labeling step. If the anti-αGal IgY antibodies are not conjugated, then a secondary labeling step is necessary with anti-IgY antibodies conjugated to either ferromagnetic beads or a fluorophore. Cells labeled with ferromagnetic microbeads can be separated using magnetic cell separation columns. In this column, cells that do not express the αGT marker gene will flow through and cells that express the αGT marker gene will be retained in the column and can be subsequently eluted by removing the magnet. If the secondary antibody or streptavidin is conjugated to a fluorophore, cells can be separated by FACS. FIG. 1B shows another embodiment of the separation system. In this embodiment, the anti-αGal IgY is directly conjugated to either ferromagnetic microbeads or a fluorophore. In this way, only one labeling step is needed to separate cells by magnetic column separations or FACS based on their αGT expression.

FIG. 2: Nucleotide sequence of the murine αGT cDNA. (SEQ ID NO:1) The coding region is indicated in bold letters.

FIG. 3: Amino acid sequence of the murine αGT. (SEQ ID NO:2)

DETAILED DESCRIPTION OF THE PREFERRED EMBODIMENT

Figure 1A:
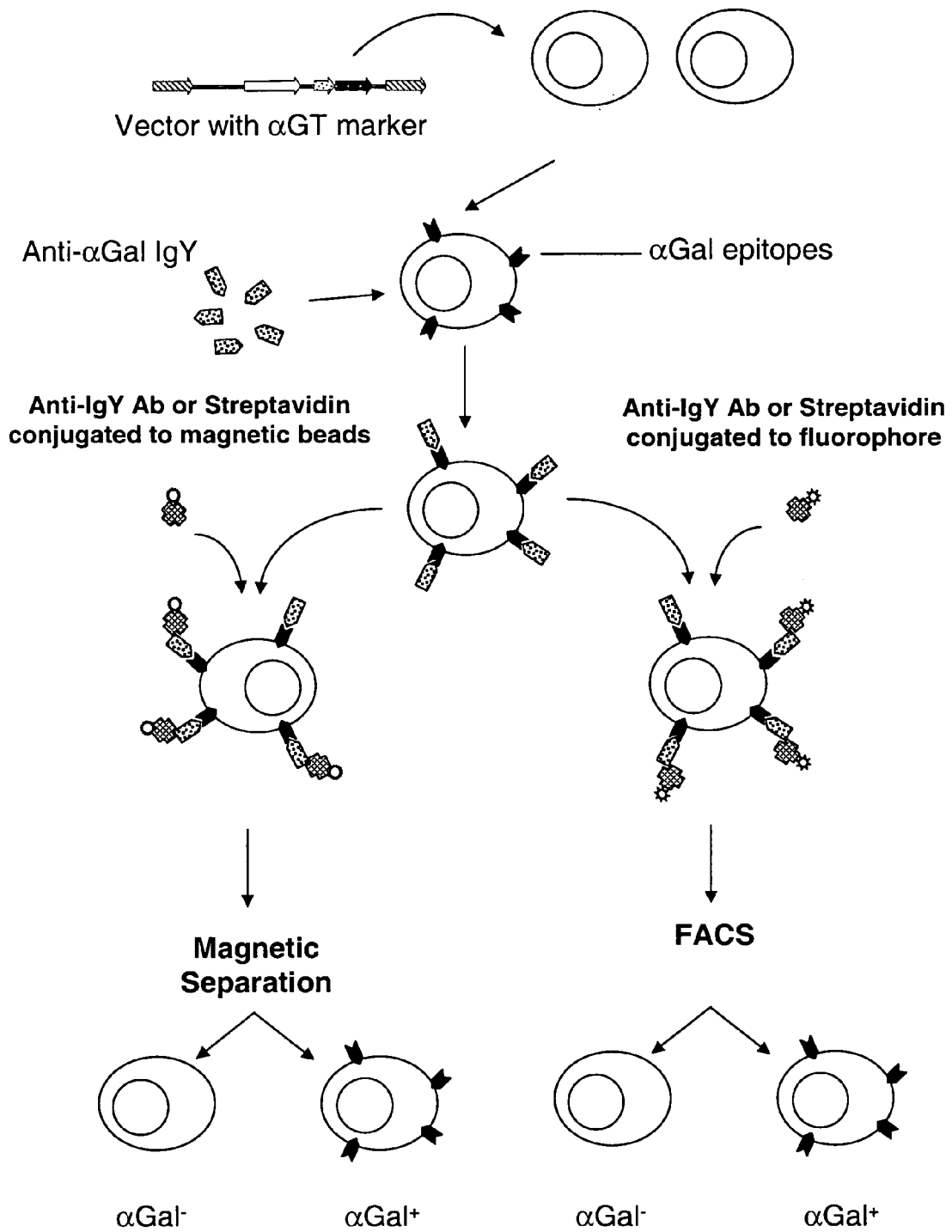
FIGS. 1A–1B: Schematics of the method of the invention.

The present invention describes a rapid method for the isolation of genetically modified cells using a novel selectable marker gene that introduces cell surface epitopes. This cell-surface marker is the αGal carbohydrate epitope which is created by the introduction of the αGT enzyme into αGal-negative cells. αGT synthesizes the linear trisaccharide α-D-Galactosyl-(1-3)-β-D-Galactosyl-(1,4)-β-N-acetylglucosaminyl-R from a β-D-Galactosyl (1,4)-β-N-acetylglucosaminyl-R precursor that is bound to glycoproteins through either N- or O-linked glycosylation. The enzyme activity of the αGT is absent in cells from humans, other old world primates and birds (Link, C. J., et al., Cancer Gene Therapy, ed. Habib Kluwer Academic, NY, 2000: 217–225; Bouhours, J. F., et al., Glycoconjugate J. 1998, 15: 93–99.). Though evolutionarily conserved, the absence of the αGT enzyme in the aforementioned species is due to a mutation in the gene which leads to the generation of a non-functional protein. However, the generation of experimental pigs and mice lacking the αGT loci, demonstrates that the loss of αGT activity does not appear to interfere with the development, fertility or general health of the animals (Thall, A. D., et al., J Biol Chem. 1995, 270(37):21437–40). Furthermore, the introduction of αGT into αGT-negative cells does not appear to have any effects on rate of proliferation or the expression of a number of phenotypic cell markers (T. DiColandrea, unpublished observations). Thus, the use of the carbohydrate epitope, αGal creates a unique marker that unlike other known cell surface proteins, does not appear to mediate phenotypic changes in the cell.

The expression of this marker can be detected by binding with a specific anti-αGal antibody or by the binding of a lectin from *Griffonia simplicifolia* B4 (IB4, Link, C. J., et al., Anticancer Research. 1998, 18: 2301–2308). These molecules can be directly or indirectly conjugated to fluorophores or magnetic particles to mediate staining, or separation of the cells expressing this selectable marker by FACS or magnetic panning techniques.

In addition, the αGal epitope is generated catalytically and added to a wide number of cell surface proteins and lipids, which makes it a very sensitive surface marker. This marker can also be tailored to selectively identify and isolate live cells of a particular phenotype within a tissue. The αGal marker can be coupled to a cell-specific phenotype by regulating the expression of the αGT enzyme using a tissue-specific or cell-specific promoter. Live cells of a particular phenotype can then be isolated in instances where no suitable cell surface marker is present to enable the live, real-time detection of these cells, such as in the case of isolating stem cells or cancer cells from freshly disaggregated αGal-negative tissues. Thus this invention also has relevance to the fields of diagnostic medicine and tissue engineering.

In the present invention, cells are marked with the cell surface αGal epitope in order to identify cells that express a second polynucleotide of interest within a larger population of cells subjected to gene transfer. Thus the present invention enables the isolation or identification of cells with any genotypic change.

Similarly, the present invention allows for the isolation of labeled cells with a specific phenotypic change whereby the expression of a second mRNA through the introduction of a mammalian expression vector leads to a phenotypic change in the cell which correlates with the presence of αGal epitopes on the cell surface.

The present invention can allow for the identification, isolation and capture of any αGal-negative cells that are previously phenotypically distinct due to their total gene expression profile by controlling the expression of the αGal marker in the cell by placing the transcription of the αGT mRNA under the control of a cell-specific or tissue specific promoter. Regulating the expression of the introduced recombinant DNA molecule such that it can be limited to a phenotypically-distinct subset of cells within a larger general population provides additional advantages to the live isolation of specific cell types where presently no or few adequate cell-surface markers exist. In one such embodiment, the present invention could be modified to allow for the isolation of adult epithelial stem cells from freshly disaggregated tissue. In another embodiment, the present invention could be modified to allow for the live isolation of specific tumor cells or malignant cells from freshly disaggregated tissue or tumor.

The invention can be modified to enable the capture of any αGal negative cells, including spontaneously αGal-negative cells, derived from a larger population of αGal positive cells for any purpose. Examples of such purposes would include the isolation of gonadal cells, at any stage of maturity, and embryonic cells, including embryonic stem cells, for the creation of homozygous knock-out mammals that would no longer express the αGT gene and therefore might be useful in clinical sciences for the study of xenotransplantation models such as in pigs and mice. The negative selection of cells which have been modified to no longer express αGal in animal cells due to modification of gene expression through gene knock-out, expression of αGT antisense RNA, siRNA, or ribozymes that target the αGT mRNA is achieved by the removal of cells expressing αGal by the binding of a polyclonal antibody against αGal epitopes and the recovery of cells which do not bind the antibody. This can be accomplished by magnetic panning techniques, FACS or by complement-mediated lysis of cells that bind the antibody. Such an embodiment can be used to screen both heterozygous and homozygous embryonic knockout cells and germline oocytes and spermatozoa in mammals. Also, development of mouse tumor cell lines that are negative for αGal expression for tumor vaccination studies in αGT knockout mice would be a useful application of a negative selection approach for αGT expression.

Figure 1B:
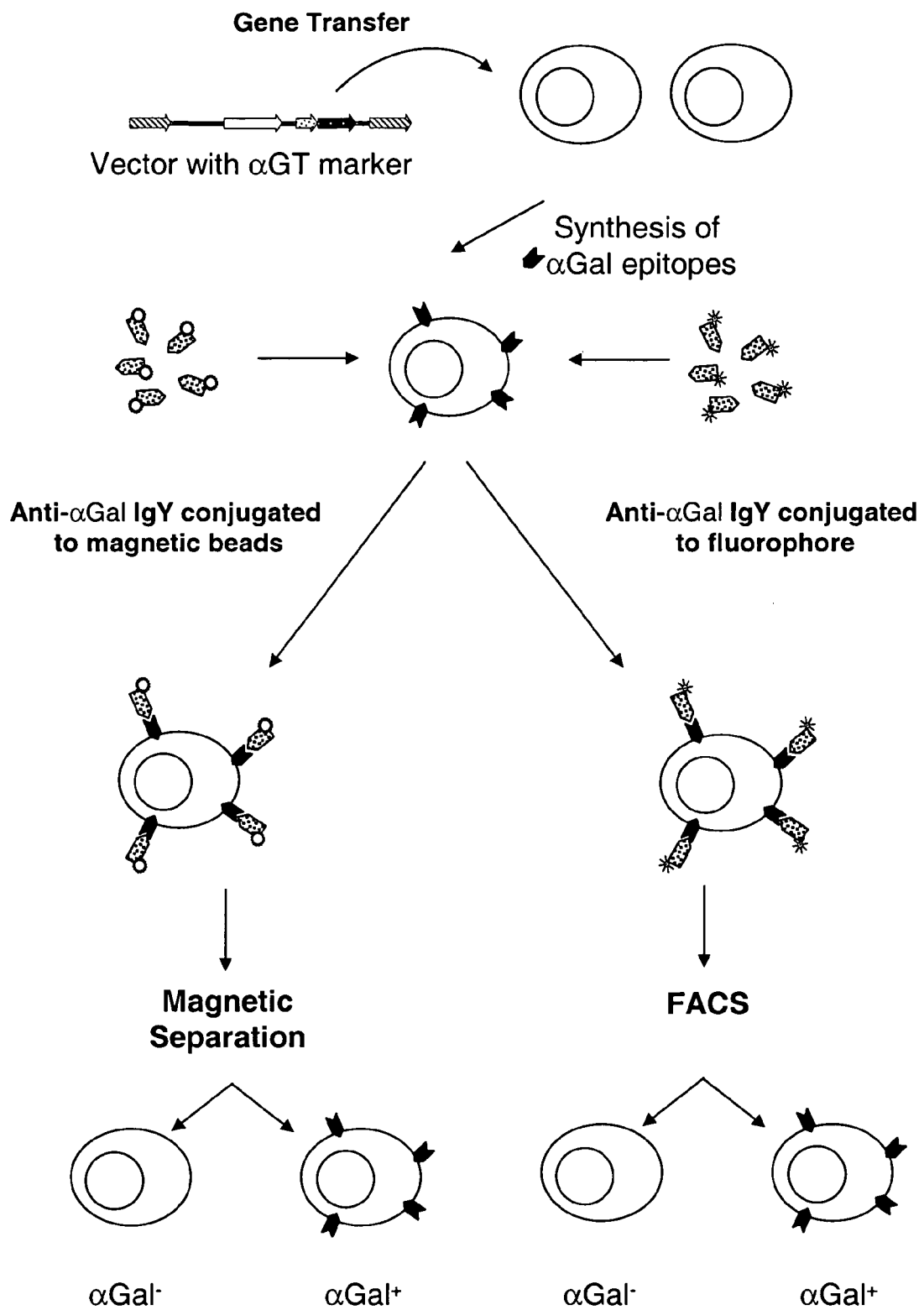

The preferred methodology for the generation of a rapid selectable marker system for the isolation of modified cells of interest can be described in four steps (FIG. 1). The first step of the method is the construction of the gene expression cassettes and the vector delivery system. The second step is the transfer of the vector encoding the gene of interest and the expression cassette encoding αGT to the target cell population. The third step is the incubation of the cells subjected to gene transfer with a reagent that bind to the αGal epitopes present on the cell surface. And finally, the fourth step of the method is the separation of αGal-positive cells from αGal-negative cells by fluorescence activated cell sorting or by magnetic panning techniques.

The expression cassette consists of a heterologous promoter driving the expression of αGT gene. FIGS. 2 and 3 show the nucleotide and sequence of the murine αGT which can be used for this purpose. The promoter driving the expression of αGT can display constitutive, regulated or tissue-specific activity in the target cell line of interest. Examples of promoters that can drive the expression of αGT in αGal-negative mammalian cells include, but are not limited to, MoMLV retroviral LTR, the SV40 promoter, the human cytomegalovirus (CMV) promoter described in Miller, et al., [Biotechniques, Vol. 7, No. 9, 980–990 (1989)], the human PGK promoter, or any other promoter (e.g., cellular promoters such as eukaryotic cellular promoters including, but not limited to, the histone promoter, RNA pol II-dependent promoter). Other viral promoters that may be employed include, but are not limited to, adenovirus promoters, HSV TK promoters, and B19 parvovirus promoters. In another embodiment the invention comprises an inducible promoter. One such promoter is the tetracycline-controlled transactivator (tTA)-responsive promoter (tet system), a prokaryotic inducible promoter system which has been adapted for use in mammalian cells. See, Paulus, W. et al., "Self-Contained, Tetracycline-Regulated Retroviral Vector System for Gene Delivery to Mammalian Cells", J of Virology, January. 1996, Vol. 70, No. 1, pp. 62–67. The selection of a suitable promoter will be evident to those skilled in the art from the teachings contained herein. Additionally, expression of αGT can be linked to the expression of the main gene of interest by including it as part of a bi-cistronic messenger RNA joined by an internal ribosome entry site (IRES).

Figure 4:
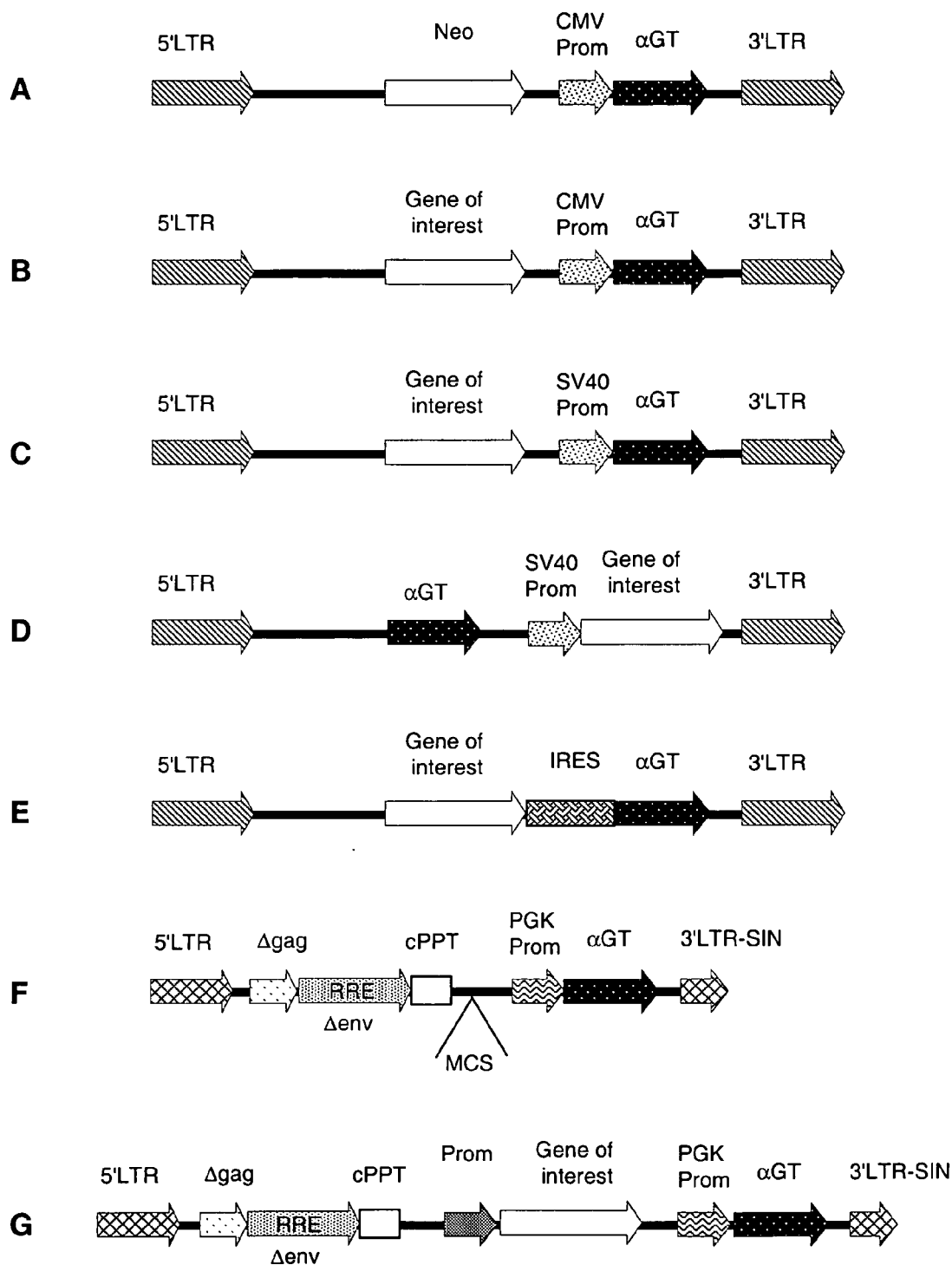
FIGS. 4A–4G: Examples of mammalian retroviral expression vector constructs that can be used to introduce αGT cDNA for the expression of αGal epitopes along with any other DNA sequence of interest. A: vector pLNCKG is described in Example 1. This vector is derived from the plasmid pLNCX and expresses αGT off the CMV promoter. B: a gene of interest can be cloned in place of the Neo gene in pLNCKG and its expression be controlled by the 5' LTR promoter. C: is an example of the same vector as in B, with a different promoter driving the expression of the selectable marker αGT. D: The αGT can be controlled by the 5' LTR promoter and the expression cassette with the gene of interest can be cloned downstream. E: Expression of the selectable marker αGT can be operably linked to the expression of the gene of interest by creating a bicistronic transcript linked through an internal ribosome entry site (IRES). F: example of an HIV-1 self inactivating retroviral vector where the expression of the selectable marker αGT is driven by the human PGK promoter. This vector (pHSPA), has a multiple cloning site that allows cloning of an expression cassette with any gene of interest. G: Example of an HIV-1 self-inactivating retroviral vector that bears to expression cassettes, one that drives the expression of any gene of interest and a second one that drives the expression of the selectable marker αGT.

The expression cassette encoding αGT forms part of an expression vector that also controls the expression of the transgene of interest. Examples of expression vectors that allow selection of transduced cells using αGT as a selectable expression marker are shown in FIG. 4. The methods for construction of viral or non-viral expression vectors for the expression and selection of αGT positive cells from αGT-negative cells are well known to those skilled in the art. Basically, any viral or non-viral vector described in the literature that uses selectable marker genes such as neomycin phosphotransferase gene ($Neo^R$), beta-galactosidase (β-Gal), puromycin acetyltransferase ($Puro^R$) or green fluorescent protein (GFP), can be utilized, by replacing such marker gene by αGT.

In one embodiment, the expression vector is a viral vector. Viral vectors which may be employed include, but are not limited to, retroviral vectors, adenovirus vectors, Herpes virus vectors, and adeno-associated virus vectors. Viral vector mediated gene transfer involves the construction of synthetic virus particles (vectors) that lack pathogenic functions which are incapable of replication, which contain a gene of interest within the viral genome and which deliver this gene to cells by the process of infection.

One of the viral vectors which have achieved the most success and attention is a retroviral vector. The prototype for a retroviral mediated gene transfer is a retroviral vector derived from Moloney Murine Leukemia Virus (MoMLV). Examples of other retroviral vectors that may be employed include, but are not limited to, spleen necrosis virus, and vectors derived from Rous Sarcoma Virus, Harvey Sarcoma Virus, avian leukosis virus, human immunodeficiency virus, myeloproliferative sarcoma virus, and mammary tumor virus. Retroviral vectors have several properties that make them useful for gene transfer. First is the ability to construct a "defective" virus particle that contains the gene of interest and is capable of infecting cells but lacks viral genes and expresses no viral gene products. The MoMLV genome encodes the polyproteins gag, pol, and env that together constitute a retroviral particle. The gag and pol genes encode the inner core of the retrovirus as well as the enzymes required for processing the retroviral gene after infection of the target cell. The env gene forms the outer envelope of the virus and recognizes a specific receptor on target cells. To construct a retroviral vector the sequences encoding the viral proteins (Gag, Pol and Env) are integrated into a packaging cell line, and separated from the sequences necessary for transcription, packaging, reverse transcription and integration (5'LTRs, psi, PPT, 3'LTR). Retroviral vectors are capable of permanently integrating the genes they carry into the chromosomes of the target cell at random positions. Murine retroviral vectors are generally produced at titers ($10^5$–$10^6$ cfu/ml) and can accommodate an insert of about 7.5 kb of heterologous sequence. The genes of interest can be incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter. In one embodiment, the retroviral vector may be one of a series of vectors described in Bender, et al., J. Virol. 61:1639–1649 (1987), based on the N2 vector (Armentano, et al., J. Virol., 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, the natural ATG start codon of gag was altered by site-directed mutagenesis to TAG, thereby eliminating unintended protein synthesis from that point. The vector LNL6 was made, which incorporated both the altered ATG of LNL-XHC and the 5' portion of MoMuSV which obviates the expression of the amino terminal of pPr80ogag. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., Biotechniques, 7:980–990, 1989). Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3). In one embodiment, the retroviral vector may be a MoMLV of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragment or truncations thereof, are not expressed.

In a preferred embodiment, a retroviral vector packaging cell line is transduced with a retroviral vector containing the nucleic acid sequence encoding the protein of interest. The viral particles produced by the packaging cell line are harvested and used to transduce the αGal negative target cells. Examples of packaging cells which may be transfected include, but are not limited to the PE501, PA317, ψ2, ψ-PAM, PA12, T19-14X, VT-19-17-H2, ψCRE, ψCRIP, GP+E-86, GP+envAM12, DAN and AMIZ cell lines. Methods for transfecting the retroviral vector DNA into retroviral packaging cell lines include, but are not limited to, electroporation, the use of liposomes, and calcium phosphate co-precipitation.

In another embodiment, the retroviral vectors can be based on human immunodeficiency virus Type I, using backbones for vector and helper packaging plasmids as described by Naldini et al, Science 1996, 272: 263–267; Zufferey et al., Nature Biotechnology 1997, 15: 871–875; and Reiser et al., Proc. Natl. Acad. Sci. USA 1996, 93: 15266–15271. Moreover, these vectors can withstand a deletion in the 3' U3 region of the 3' LTR that turns them into self-inactivating vectors after integration into the target genome, without a negative impact in vector titers (Zufferey et al., J of Virology 1998, 72: 9873–9880; Miyoshi et al., J. of Virology 1998, 72: 8150–8157). Lentiviral vectors pseudotyped with the VSV-G envelope have the additional advantage of wide tropism and high efficiency of infection of dividing and non-dividing cells. Also, they can be produced at high titers ($5 \times 10^6$–$10^7$ tu/ml) and have a larger cloning capacity of murine retroviral vectors.

Viral vectors based on adenovirus have recently proven effective as vehicles for gene transfer in vitro and in vivo in several cell types. Adenoviral vectors are constructed using a deleted adenoviral genome that lacks either the E3 gene region and/or the E1 gene region that is required for producing a replicating adenovirus particle. Recombinant genes are inserted into the site of the deleted gene region(s). Adenoviral particles are then produced in a cell line that is able to express E1 or E3 genes and thus capable of assembling a viral particle which contains only the recombinant viral genome with the therapeutic gene. Adenoviral vectors differ from retroviral vectors in that they do not integrate their genes into the target cell chromosome. Adenoviral vectors will infect a wide variety of both dividing and non-dividing cells in vitro and in vivo with a high level of efficiency providing expression of their recombinant gene for a period of several weeks to months. Adenoviral vectors can be produced at high titer of $10^{10}$–$10^{11}$ cfu/ml and have a maximum cloning capacity of 7,000 bp.

Other viruses exhibit properties that may be useful as potential vectors for gene transfer. One such virus is the adeno-associated virus vector. Like the retrovirus, it can provide a completely defective vector that permanently integrates in the chromosome of the target cell. This adenoviral vector integrates at a predictable location within the affected cell and could make this type of vector safer than those that integrate randomly into the genome.

Another viral vector is based on the Herpes Simplex virus, which is capable of infecting cells and persisting indefinitely in a latent state. The recombinant virus can infect dividing and non-dividing cells and has a theoretical maximum cloning capacity of up to 150 kb. Self-maintaining HSV anplicons have been designed that ensure continued replication of the episomal vector along with cell division and has been already used to transfer the αGT gene to mammalian cells ["A novel herpes virus amplicon system for in vivo gene delivery" by Wang S et al., Gene Therapy. 1997 Nov; 4(11):1132–41; "Eliciting hyperacute rejection as a tumor killing strategy. Herpes amplicon vector transfer of the αGT gene" by Link C. J, et al., Adv Exp Med Biol. 2000; 465:217–27].

The second step in the methodology of the present invention is the introduction of mammalian expression vector constructs to the cells and/or disaggregated tissue. The introduction of gene expression vectors to cells is derived from procedures well known to those skilled in the art. Briefly, in one example, retroviral vectors can be transduced into the target cell of interest by incubation of these cells with the viral vector particles obtained from the supernatant of retroviral packaging cell lines. During transduction, the supernatant collected from the packaging cells is incubated with the target cells for 12–24 hours. Then, 24–48 hours later, the target cells are checked for the expression of the αGal epitope on the cell surface.

The present invention can be extended to allow for the selection of cells of interest from freshly disaggregated tissue based on the introduction of the αGT marker after disaggregation has occurred. Tissues can be disaggregated using often a cocktail of matrix proteases such as collagenases and hyaluronidase in procedures which are commonly known to those skilled in the art. Cells are subsequently isolated away from stromal tissue and matrix through various methods which include separation by cell density and by cell size. The supernatant from the packaging cells would then be incubated with cells isolated from the freshly disaggregated tissue in the same manner as described above.

The third step of the method involves the identification of the cells expressing αGT in order to differentiate them from the cells that do not express αGT. This can be accomplished by the use antibodies that recognize the αGal epitopes on the cell surface or by the use of a lectin obtained from Griffonia simplicifolia isolectin B4 ["Facile preparation of the alpha-Gal-recognizing Griffonia simplicifolia I-B4 isolectin", Winter H C, Goldstein I J, Carbohydr Res. 2004 Jan 2; 339(1):153–5; "Enzyme-linked lectin assay (ELLA): use of alkaline phosphatase-conjugated Griffonia simplicifolia B4 isolectin for the detection of alpha-D-galactopyranosyl end groups", McCoy J P Jr, Varani J, Goldstein I J, Anal Biochem. 1983 Apr 15, 130(2): 437–44; "Griffonia simplicifolia I isolectin as a functionally monovalent probe for use in flow cytometry" McCoy J P Jr, Shibuya N, Riedy M C, Goldstein I J, Cytometry. 1986 Mar, 7(2):142–6] that recognizes αGal epitopes. The antibodies can be obtained from any animal and can be of polyclonal or monoclonal origin. However, due to the fact that most animal species used to derive monoclonal and polyclonal antibodies are positive for αGT, they are not likely to develop high titers of anti-αGal antibodies. Therefore, the immunization of chickens to obtain polyclonal anti-αGal antibodies from egg yolk is the preferred method of choice ["Characterization of a polyclonal anti-Galalphal-3Gal antibody from chicken" Bouhours J F et al., Glycoconj J. 1998 Jan; 15(1):93–9]. The antibodies or IB4 lectin can be directly labeled with a fluorophore or with biotin, or they can be indirectly labeled with a secondary antibody conjugated to fluorescent molecules or biotin.

The fourth and final separation step in this procedure separates the αGal positive cells away from the population of αGal negative cells. This separation can be achieved by more than one method. In the first method, the cells are first bound with the anti-αGal chicken antibody composition. Next the cells are incubated with an anti-chicken antibody that is conjugated with biotin. Then, the cells are bound with anti-biotin magnetic microbeads and are passed over a commercial magnetic column (Miltenyi Biotech). Cells actually bound by all three components are trapped by the column and can be eluted by removing the magnet. In the second method, cells are first stained with the anti-αGal chicken antibody composition and then bound with a secondary antibody that recognizes the chicken antibody composition and is itself labeled with a fluorophore. Cells are then passed through a FACS sorter and isolated by the selective labeling derived from the presence of αGal epitopes on the cell surface. Alternatively, the anti-αGal chicken antibody composition can be modified for the direct isolation of αGT positive cells by directly conjugating it either to a fluorophore, to a biotin label, or to ferromagnetic beads. In another set of embodiments, the antibody can be substituted with the isolectin IB4, which can be directly conjugated to a fluorophore or magnetic microbeads, for FACS or magnetic column separation, respectively. Also the isolectin IB4 can be indirectly labeled with a biotinylated anti-IB4 antibody, or with a fluorophore-conjugated anti-IB4 antibody for FACS separation or with anti-IB4 conjugated to ferromagnetic microbeads for subsequent magnetic column separation.

EXAMPLES

Example 1

Production of Retroviral Vector Expressing αGT, pLNCKG

In one embodiment of the present invention, the method for the rapid isolation of cells via the labeling of these cells with the αGal epitope was investigated by placing the αGT cDNA in a mammalian expression vector derived from DNA sequences of murine retroviruses, called pLNCKG. To construct this vector, A 1,077 bp fragment of murine αGT gene was PCR amplified by a forward primer, 5'-ACAAAAGCT-TGA CATGGATGTCAAGGGAAAAGTAAT-3'(SEQ ID NO:3), which contains a Kozak sequence to enhance the translation of αGT, and a reverse primer, 5'-AATTATCGA TTCAGACATTATTTCTAAC-3'(SEQ ID NO:4), and then cloned into the ClaI and HindIII sites of pLNCX to produce pLNCKG retroviral vector (FIG. 4). This vector was transfected into the packaging cell line 293.AMIZ to generate the vector producer cell line 293.AMIZ/LNCKG ["Chimeric retroviral helper virus and picomavirus IRES sequence to eliminate DNA methylation for improved retroviral packaging cells", Young and Link, J. Virol. (2000) 74: 5242–5249]. Transfected cells were selected in presence of G418 and ZEOCIN™ antibiotic for two weeks. Mixed population of selected cells was subcloned by limiting dilutions. Single cell-derived VPC were screened for their ability to effectively transduce human epithelial cancer cell lines established from different tissues. The clone which supernatant consistently yielded highest transduction efficiency and αGT expression on a panel of human epithelial cancer cell lines was identified and designated 293Z.CKG VPC. A master cell bank, working cell bank and production lot was generated for 293Z.CKG VPC was originated from one vial of the seed bank, expanded in flasks at 37° C.±1° C. in 5% ±1% $CO_2$. The culture medium was RPMI-1640 supplemented with 10% fetal bovine serum (FBS) and 2mm L-glutamine. When the 293Z.CKG VPC reached sufficient density, the culture fluids (supernatant) are harvested, filtered, and pooled into a sterile container. The fill bottles are frozen and stored at or below –60° C. Retrovirus-containing supematants from 293Z.CKG VPC were used to transduce different human cancer cell lines (mentioned in examples below).

Example 2

Transduction of A375 Cells with Vectors Encoding αGT.

To generate αGal$^{(+)}$-A375 cells, 2×10$^6$ A375 cells were transduced with 2 mL of supernatant containing the LNCKG retrovirus with an infectious titer of 2×10$^6$ tu/mL. Cells were selected for resistance to Neomycin by a two-week selection in medium supplemented with G418 1 mg/mL. After this period of selection, cells were stained for expression of the αGal epitope with a chicken anti-αGal polyclonal antibody and sorted by fluorescence activated cell sorting. These A375-αGT$^+$ cells were used below in mixes of A375-αGT$^+$ and A375 cells performed at different ratios to test and optimize the procedure of separation of αGT positive from αGT negative cells. Also, A375-LNCKG clone was used as a standard to test different batches of affinity purified anti-αGal IgY.

Example 3

Purification of Anti-αGal Polyclonal Chicken Antibody

The isolation of cells expressing αGT by the present invention requires the use of the antibody composition mentioned above. The antibody composition comprises a population of the affinity purified IgY molecules that specifically and accurately recognize the αGal cell surface epitopes. The antibody composition was created by the immunization of a White Leghorn chicken with an antigen comprised of αGal epitopes conjugated to BSA. The immunization scheme was 4 injections of the αGal-BSA over a period of 4 weeks followed by a booster injection once every 4–6 weeks. Total IgY was purified from the chicken egg in groups of 6 eggs per purification. The purification of the total IgY can be completed according to several techniques known to those skilled in the art. One such method of purification involves the extraction of IgY from the egg yolk using deionized water followed by diluting the egg yolk 1:10 in cold 3 mM HCl so that the pH of the final suspension is 5. Proteins are then precipitated from the clarified suspension using 60% saturation with ammonium sulfate. The precipitate is centrifuged and dissolved in 50 mM phosphate pH 7.4, 0.5 M sodium sulfate. The dissolved protein is then applied to a T-gel column according to manufacturer's instructions (Pierce) and the IgY is eluted with 50 mM phosphate pH 7.4. In another example, total IgY immunoglobulin can be extracted from egg yolk using a commercially available EGGSTRACT™ kit (Promega) whereby the IgY is isolated on the basis of first removing the lipid fraction from the yolk followed by precipitation of the IgY immunoglobulins. After isolation of total IgY, purity of the collected IgY fraction is determined by polyacrylamide gel electrophoresis (SDS-PAGE). This total IgY fraction is then used to purify the antibody composition of IgY directed against the αGal epitopes by affinity chromatography. In this method, the total IgY fraction is passed over a column of affinity resin containing αGal disaccharides linked directly to an agarose resin (Calbiochem). In another variation of the method, the total IgY fraction is passed over a column of affinity resin containing αGal-BSA, which is directly conjugated to CNBr-activated Sepharose 4 FastFlow (Pharmacia Biotech). In this case, the affinity resin is created by mixing pure synthesized αGal-BSA (Vector Labs) with Sepharose 4 FastFlow beads which have been pre-equilibrated according to the manufacturer's instructions. Then, 300 μg of resin is mixed with 1 mg of αGal-BSA in 1 ml of Phosphate Buffered Saline (PBS) overnight at 4° C. The resin is washed 3 times with copious amount of PBS and incubated with 10 ml of 100 mM ethanolamine (pH 7.5) for 4 hours on a rotating wheel at room temperature. The resin is then washed 2 times with PBS and stored in PBS with 0.01% merthiolate at 4° C. until use.

The affinity resins for a 10 ml column are washed with 5 column volumes of 10 mM TrisHCl pH 7.5. Then the loaded resins are washed with 5 column volumes of 100 mM Glycine pH 2.5 and then washed with 10 column volumes of 10 mM TrisHCl pH 7.5 until the flow-through wash buffer is at pH 7.5. The total IgY fraction is bound in batch to the resins by mixing 5 ml of total IgY fraction with the 10 ml of prepared affinity resins on a rotating wheel at 4° C. overnight in a total volume of 40 ml.

The batch bound resin is then loaded onto a 10 ml column and washed with 20 column volumes of 10 mM TrisHCl pH 7.5 followed by 5 column volumes of 50 mM NaCl, 10 mM TrisHCl pH 7.5. Then the column is washed with 10 column volumes of 10 mM TrisHCl pH 7.5 before eluting the anti-αGal IgY composition with 5 column volumes of 100 mM Glycine pH 2.5. Fractions of the eluent are collected in 4–5 ml neutralized with 4 ml of 1 M TrisHCl pH 8.0. The fractions are dialyzed in PBS at 4° C. overnight. The fractions are concentrated using a Microcon spin column (Amicon) to a final concentration of 1 mg/ml. The fractions are analyzed for their purity, specificity and affinity for αGal epitopes using a modified Bradford assay, SDS-PAGE analysis, ELISA determination for the purified anti-αGal IgY against αGal versus BSA (FIG. 5), and by FACS analysis using a batch of purified anti-αGal IgY designated as the standard representative of pure anti-αGal IgY to stain a standardized clone of a cell line referred to as A375-LNCKGstd which is an αGT-negative melanoma cell line A-375 that has been modified to express the murine αGT enzyme.

Figure 5:
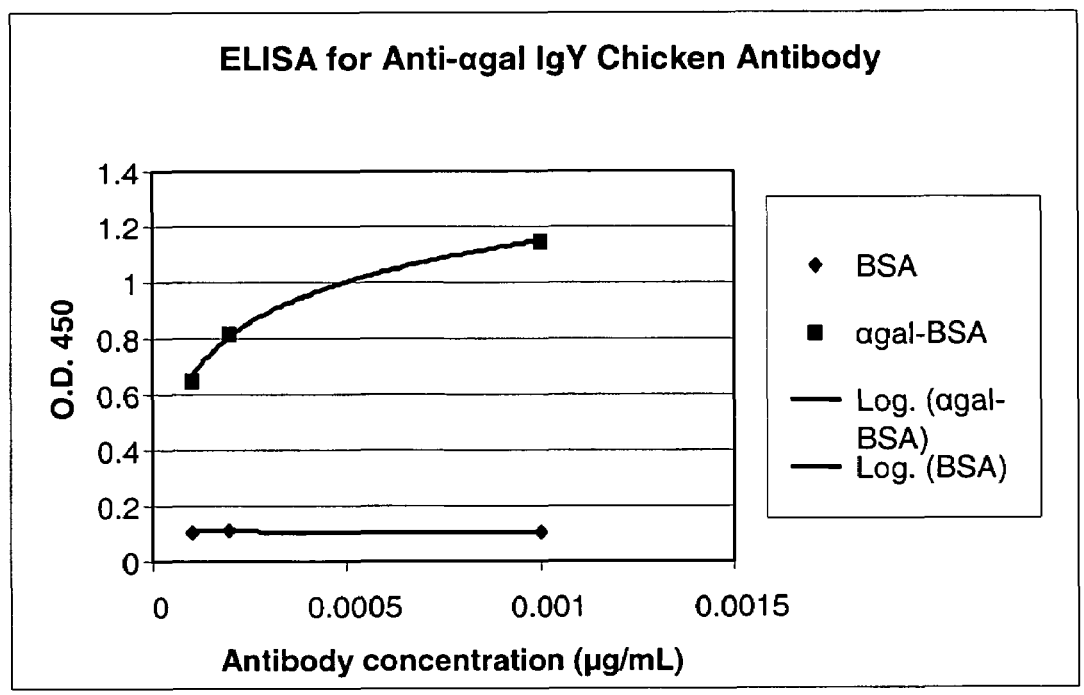
FIG. 5: Typical results of ELISA using an anti-αGal chicken antibody composition after affinity purification.

Each batch of anti-αGal chicken antibody composition is tested by ELISA to examine the specificity of the composition for αGal epitopes versus the entire immunogen, αGal-BSA. The ELISA is performed by first coating two 96 well plates with 30 μL of a 1 mg/mL solution of αGal-BSA diluted in a 0.05 M bicarbonate buffer solution. The plates are incubated in an 8% $CO_2$ incubator overnight. The plates are then washed three times with PBS-Tween 0.05% and washed twice with 100 μL of Superblock (Pierce). The plates are then incubated in Superblock for 30 min at room temperature. A solution of 100 μL of primary antibody (1:1000 dilution of purified anti-αGal IgY) is added to the plates and the plates are incubated at 4° C. overnight. The plates are then washed three times with PBS-Tween 0.05% and twice with 100 μL of Superblock. The plates are incubated in Superblock for 30 min at room temperature. Then, 100 μL of secondary antibody, rabbit anti-chicken conjugated to peroxidase is added and the plates are incubated at room temperature for 1 hour. The plates are washed 5× in PBS-Tween 0.05%. The TMB substrate (100 μtL) is added of TMB for about 10 minutes. One hundred μL of 0.5% sulfuric acid is then added to stop the reaction. The OD is read at 450 nm. The ELISA curve was originally derived with numerous dilutions of the primary antibody over several logs of concentration. As the various batches display a tight and reproducible ELISA curve, we have since performed ELISA with 3 standard dilutions. Results from one anti-αGal chicken antibody composition batch are shown in FIG. 5.

Example 4

Labeling of Cells Expressing αGT with Purified Anti-αGal IgY

The purified anti-αGal IgY antibody composition was used to label human melanoma A375 cells transduced with vector pLNCKG in example 2. The method begins with the staining of live cells of interest is as follows:

1) Treat cells with trypsin as normal for A375 until cells are disaggregated into single cell suspension
2) Halt trypsinization with 0.25 volumes of soybean trypsin inhibitor
3) Spin down cells and resuspend in either 1% Fish skin gelatin (FSG) or 0.5% BSA, 2 mM EDTA
4) Wash cells twice, and resuspend cells in 1.5 ml at 1–10 million/ml.
5) Add 1.5 μl of primary antibody: purified anti-αGal IgY (1:1000 dilution) and incubate on ice 1 hr.

6) Wash with resuspension buffer and resuspend in 1.5 ml
7) Add 1.5 µl of secondary biotinylated rabbit anti-chicken IgY (1:1000 final dilution) and incubate 30 min at room temperature
8) Wash cells twice with 10 ml PBS and resuspend in 1 ml of PBS
9) Add 1 µl of streptavidin conjugated to phycoerythrin fluor to create a final dilution of 1:1000 (1 µg–2 µg/ml)
10) Incubate for 15 minutes at room temperature in the dark.
11) Wash cells with 10 ml PBS and resuspend in 1 ml of PBS.

Figure 6:
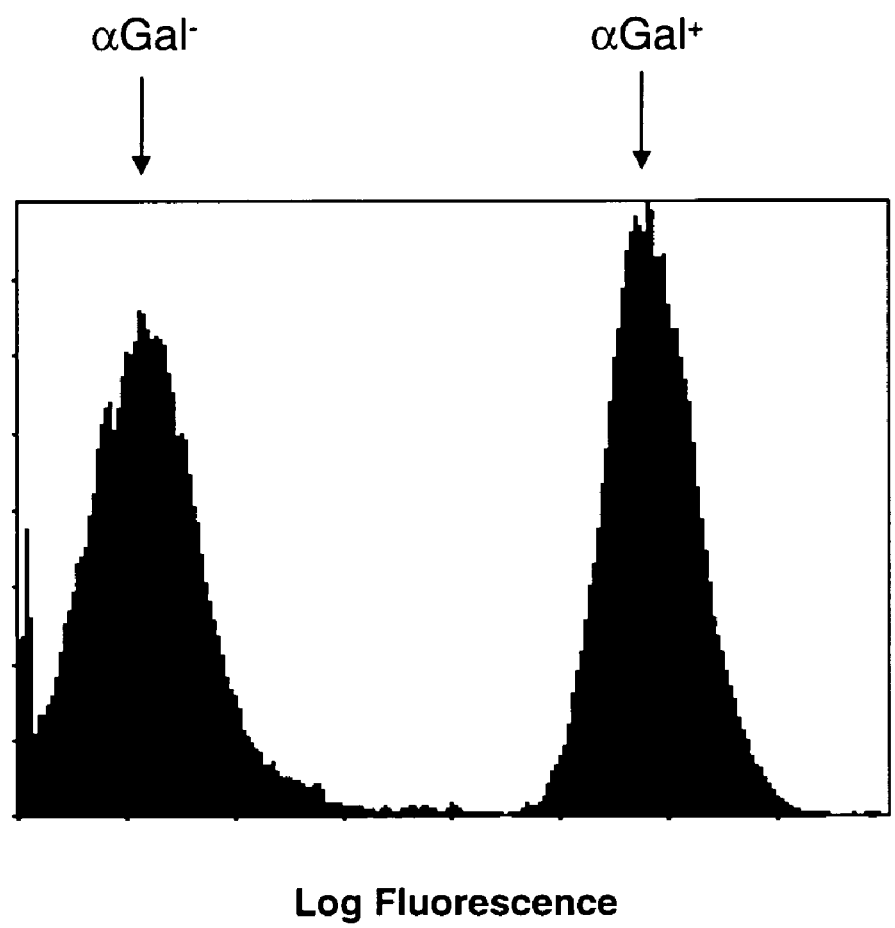
FIG. 6: FACS analysis of A375 cells modified to express αGT (A375-LNCKG) and stained with the anti-αGal chicken antibody composition versus the parental αGal-negative A375 control cells. To perform this analysis, αGT (+) cells were first stained with an affinity purified anti-αGal IgY chicken primary antibody, then stained with a biotinylated mouse anti-IgY secondary antibody and a third labeling step with streptavidin conjugated to phycoerythrin.

The cells were analyzed by FACS and compared to A375 cells that did not contain LNCKG (FIG. 6). The distance between the means of both peaks also allows for an accurate separation of αGal-positive cells from the negative parental cell line, A375.

Example 5

Magnetic Separation of αGal+ Cells

In the second example, the LNCKG vector containing the αGT cDNA was introduced into A375-GFP cells using the transduction methods described previously. The subsequent αGal$^{(+)}$/GFP$^{(+)}$ cells were stained with purified anti-αGal IgY antibody and sorted to a pure population of αGal$^{(+)}$/GFP$^{(+)}$ cells by FACS. These αGal(+)/GFP(+) A375-cells were mixed with the parental αGal$^{(-)}$/GFP$^{(-)}$ A375 cell line in various ratios (100:1; 10:1, 1:1) and examined for ability of the antibody to specifically bind and isolate αGal$^{(+)}$ cells from a larger population of αGal$^{(-)}$ cells using magnetic panning techniques. Table 1 shows the percentage of cells staining positive for αGal epitopes using the purified anti-αGal IgY in mixed populations as detected by FACS analysis prior to αGal$^{(+)}$ cell isolation by magnetic panning.

TABLE 1

FACS analysis of a population of mixed αGal$^{(+)}$/GFP$^{(+)}$ A375 cells in a larger population of αGal$^{(-)}$/GFP$^{(-)}$ A375 cells.

| Percentage of α-Gal$^+$/GFP$^+$ cells in mixed cell population | Percentage of cells staining positive for α-Gal with purified anti-αGal IgY |
|---|---|
| 100 | 99.2 |
| 50 | 50.3 |
| 10 | 12.9 |
| 1 | 9.6 |
| 0 | 4.3 |

The mixed cell populations were prepared for magnetic panning according to the following method:
1) Treat cells with trypsin as normal for A375 until cells are disaggregated into single cell suspension
2) Halt trypsinization with 0.25 volumes of soybean trypsin inhibitor
3) Spin down cells and resuspend in either 1% fish skin gelatin or 0.5% BSA, 2 mM EDTA (resuspension buffers)
4) Wash cells twice and resuspend cells in 1.5 ml at 10 million cells/ml of A375/GFP$^+$/αGal$^+$: A375
5) Add 1.5 µl of purified anti-αGal IgY (1:1000 dilution) and incubate on ice 1 hr
6) Wash with resuspension buffer and resuspend in 1.5 ml of resuspension buffer
7) Add 1.5 µl of secondary biotinylated rabbit anti-chicken (1:1000 final dilution) and incubate 30 minutes at room temperature
8) Wash twice in resuspension buffer using 10 ml each, wash and spin down at 300×g for 10 minutes to pellet gently, and resuspend cell pellet into 80 µl of resuspension buffer
9) Add 20 µl of anti-biotin microbeads and incubate 15 minutes at 6–12° C.
10) Use degassed buffer to prepare column by washing miniMACS MS column (Miltenyi Biotec) with 500 µl resuspension buffer and place column in magnetic field
11) Apply cell suspension (500 µl) to column. Allow negative cells to flow through and collect for additional column treatment.
12) Wash column 3 times with 500 µl each of degassed resuspension buffer Remove column from separator and place over a collection tube.
13) Add 1 ml resuspension buffer to column and use plunger to flush out positive cells.

The final separation step in the procedure isolates the cells of interest away from the larger general population. The cells bound with the anti-biotin microbeads are passed over a commercial magnetic column (Miltenyi Biotec), bound to the column and eluted by removing the magnet according to the following procedure: After the cells are sent through the magnetic column, the number of captured cells eluted from the column is counted. The results are shown in Table 2. In reproducible experiments at least 80% of αGal$^+$ cells are isolated from the larger population and can be eluted from the column. The captured cells were examined for GFP fluorescence and compared to fluorescence of the cells captured from the A375 parental cell line.

TABLE 2

Number of cells captured from mixed population by magnetic panning using purified anti-αGal IgY.

| Population at start | Number of captured cells | Theoretical recovery of A375 αGal$^{(+)}$ |
|---|---|---|
| 1 × 10$^7$ cells (10:1 ratio of αGal$^{(-)}$:αGal$^{(+)}$) | 1 × 10$^6$ | 1 × 10$^6$ |
| 1 × 10$^6$ cells αGal$^{(+)}$ | 8.3 × 10$^5$ | 1 × 10$^6$ |
| 1 × 10$^6$ cells αGal$^{(-)}$ | negligible | 0 |
| 1 × 10$^6$ αGal$^{(+)}$, no primary Ab | negligible | 0 |
| 1 × 10$^6$ αGal$^{(-)}$, no primary Ab | negligible | 0 |

Table 3 shows the percentage of αGal$^{(+)}$/GFP$^{(+)}$-A375 cells captured by magnetic isolation from population with different mixture ratios of αGal$^{(+)}$/GFP$^{(+)}$-A375 and αGal$^{(-)}$/GFP$^{(-)}$-A375 cell as determined by FACS analysis of GFP fluorescence of the captured cell population compared with the parental GFP$^{(-)}$ A375 cell line. This table shows that a population with 1% of αGal$^{(+)}$ cells is enriched to 60% αGal$^{(+)}$ in only one round of magnetic purification, a procedure that usually takes only 2 hours. A second round of purification can take this population to higher than 98% purity of αGal$^{(+)}$ cells and to essentially 100% purity in a third round of purification.

TABLE 3

αGal(+)/GFP(+)-A375 cells captured by magnetic isolation from populations with different mixture ratios of αGal(+)/GFP(+)-A375 and αGal(-)/GFP(-)-A375 cells.

| Percentage of αGal(+)/GFP(+)-cells in population before isolation | Percentage of αGal(+)/GFP(+) cells after magnetic capture (determined by FACS of GFP cells) |
|---|---|
| 100 | 98.5 |
| 50 | 94.75 |
| 10 | 57.77 |
| 1 | 59.63 |
| 0 | 1.2 |

What is claimed is:

1. A method for identifying host cells comprising a heterologous polynucleotide sequence, said method comprising:

introducing to a population of cells a polynucleotide construct, said polynucleotide construct comprising a heterologous polynucleotide sequence the presence of which is desired in said host cells, and a marker polynucleotide sequence which encodes an alpha-(1,3)-galactosyl (αGal) epitope conferring protein, said marker polynucleotide sequence operably linked to a promoter sequence within said polynucleotide construct operable in said host cells, wherein said αGal epitope conferring protein is N-acetyl-lactosaminide 3-apha galactosyltransferase (αGT), and wherein said population of cells in αGT negative.

2. The method of claim 1 wherein said step of detecting said αGal epitope is by an antibody which binds an αGal epitope.

3. The method of claim 1 wherein said marker polynucleotide sequence comprises the polynucleotide sequence of SEQ ID NO:1.

4. A method for selecting cells from a population of cells that have been subject to nucleotide transfer and which contain heterologous nucleotide sequences comprising:

introducing to a population of cells a polynucleotide construct, said polynucleotide construct comprising a nucleotide sequence, the presence of which is desired in a host cell, and a sequence that encodes αGT, said sequence that encodes αGT operably linked to regulatory sequences within said polynucleotide construct operable in said host cell, so that αGT is expressed in cells which contain said polynucleotide construct and thereafter separating cells which contain said polynucleotide construct from others in said population of cells based upon αGT expression, wherein said population of cells is αGT negative.

5. The method of claim 4 wherein said step of separating cells comprises the steps of:

labeling cells which express an αGal epitope synthesized as a result of said αGT expression, and, separating labeled cells from said population of cells.

6. The method of claim 5 wherein said labeled cells are labeled with an anti-αGal antibody.

7. The method of claim 6 wherein the antibody is an anti-αGal IgY antibody.

8. The method of claim 7 wherein said anti-αGal IgY antibody is obtained from chicken egg yolk from chickens immunized with bovine serum albumin (BSA)-αGal conjugates.

9. The method of claim 8 wherein said anti-αGal IgY is affinity purified in affinity columns bearing αGal epitopes.

10. The method of claim 7 where said anti-αGal IgY is conjugated with biotin.

11. The method of claim 10 wherein the biotin-conjugated anti-αGal IgY antibodies are further bound by anti-biotin secondary antibody or streptavidin covalently conjugated to a fluorescent molecule.

12. The method of claim 11 wherein cells with bound fluorescent conjugated antibodies are separated from the population by fluorescence activated cell sorting.

13. The method of claim 10 wherein the biotin-conjugated anti-αGal IgY antibodies are further bound by anti-biotin or streptavidin conjugated to ferromagnetic microbeads.

14. The method of claim 13 wherein ferromagnetic microbead labeled cells are separated from non-labeled cells by magnetic separation columns.

15. The method of claim 7 wherein said anti-αGal IgY is directly conjugated with a fluorescent molecule so that cells expressing an αGal epitope are fluorescently labeled.

16. The method of claim 15 wherein the fluorescently labeled cells are separated from the non-labeled cells by fluorescence activated cell sorting.

17. The method of claim 7 wherein said anti-αGal IgY is directly conjugated with ferromagnetic microbeads so that cells expressing an αGal epitope are magnetically labeled.

18. The method of claim 17 wherein the labeled cells are separated from non-labeled cells by magnetic separation columns.

19. The method of claim 5 where the αGal epitope expressing cells are labeled with the isolectin IB4 from *Griffonia simplicfolia*.

20. The method of claim 19 where said isolectin IB4 is directly conjugated with biotin.

21. The method of claim 20 wherein the biotin conjugated cells are bound by anti-biotin or streptavidin conjugated to ferromagnetic microbeads.

22. The methods of claim 21 wherein the labeled cells are separated from non-labeled cells by magnetic separation columns.

23. The method of claim 20 wherein the biotin conjugated cells are bound by anti-biotin secondary antibody or streptavidin covalently conjugated to a fluorescent molecule.

24. The method of claim 23 wherein fluorescently labeled cells are separated from the non-labeled cells by fluorescence activated cell sorting.

25. The method of claim 19 where said isolectin IB4 is directly conjugated with a fluorescent molecule.

26. The methods of claim 25 wherein the fluorescently labeled cells are separated from the non-labeled cells by fluorescence activated cell sorting.

27. The method of claim 19 where said isolectin IB4 is directly conjugated with ferromagnetic beads.

28. The method of claim 27 wherein the labeled cells are separated from non-labeled cells by magnetic separation columns.

29. The method of claim 5 wherein the cells are labeled with a labeling compound selected from the group consisting of: an anti αGal antibody and an isolectin IB4 from *Griffonia simplicifolia*.

30. The method of claim 29 wherein said labeling compound is further attached to a fluorescent compound for fluorescence activated sorting.

31. The method of 29 wherein said labeling compound is conjugated to ferromagnetic beads for separation using a magnetic separation column.

32. The method of claim 4 wherein said polynucleotide construct is a vector.

33. The method of claim 32 wherein said vector is a viral vector.

34. The method of claim 33 wherein said viral vector is selected from the group consisting of adenoviral vectors, retroviral vectors, lentiviral vectors, herpes-virus vectors, and adeno-associated vectors.

* * * * *

UNITED STATES PATENT AND TRADEMARK OFFICE
CERTIFICATE OF CORRECTION

PATENT NO. : 7,078,179 B2 Page 1 of 1
APPLICATION NO. : 10/838750
DATED : July 18, 2006
INVENTOR(S) : Dicolandrea et al.

It is certified that error appears in the above-identified patent and that said Letters Patent is hereby corrected as shown below:

Claim 22, Col. 30, lines 62:
DELETE:
after The "methods"
ADD:
after The --method--

Signed and Sealed this

Third Day of October, 2006

JON W. DUDAS
*Director of the United States Patent and Trademark Office*

SEQUENCE LISTING

<160> NUMBER OF SEQ ID NOS: 4

<210> SEQ ID NO 1
<211> LENGTH: 3450
<212> TYPE: DNA
<213> ORGANISM: Mus musculus

<400> SEQUENCE: 1

```
cgtcttagga ggctggagat tctgggtgga gccctagccc tgccttttct tagctggctg      60
acaccttccc ttgtagactc ttcttggaat gagaagtacc gattctgctg aagacctcgc     120
gctctcaggc tctgggagtt ggaaccctgt accttccttt cctctgctga gccctgcctc     180
cttcggcagg ccagagctcg acagaagctc ggttgctttg ctgtttgctt tggagggaac     240
acagctgacg atgaggctga ctttgaactc aagagatctg cttacccag tctcctggaa      300
ttaaaggcct gtactacctt gcctggacct aagattttca tgatcactat gcttcaagat     360
ctccatgtca acaagatctc catgtcaaga tccaagtcag aaacaagtct tccatcctca     420
agatctggat cacaggagaa aataatgaat gtcaagggaa aagtaatcct gttgatgctg     480
attgtctcaa ccgtggttgt cgtgttttgg aatatgtca acagcccaga cggctctttc      540
ttgtggatat atcacacaaa aattccagag gttggtgaga acagatggca gaaggactgg     600
tggttcccaa gctggtttaa aaatgggacc cacagttatc aagaagacaa cgtagaagga     660
cggagagaaa agggtagaaa tggagatcgc attgaagagc ctcagctatg ggactggttc     720
aatccaaaga accgcccgga tgttttgaca gtgaccccgt ggaaggcgcc gattgtgtgg     780
gaaggcactt atgacacagc tctgctggaa aagtactacg ccacacagaa actcactgtg     840
gggctgacag tgtttgctgt gggaaagtac attgagcatt acttagaaga ctttctggag     900
tctgctgaca tgtacttcat ggttggccat cgggtcatat tttacgtcat gatagatgac     960
acctcccgga tgcctgtcgt gcacctgaac cctctacatt ccttacaagt ctttgagatc    1020
aggtctgaga agaggtggca ggatatcagc atgatgcgca tgaagaccat tggggagcac    1080
atcctggccc acatccagca cgaggtcgac ttcctcttct gcatggacgt ggatcaagtc    1140
tttcaagaca acttcgggt ggaaactctg gccagctgg tagcacagct ccaggcctgg     1200
tggtacaagg ccagtcccga gaagttcacc tatgagaggc gggaactgtc ggccgcgtac    1260
attccattcg gagaggggga tttttactac cacgcggcca ttttttggagg aacgcctact    1320
```

```
cacattctca acctcaccag ggagtgcttt aagggatcc tccaggacaa gaaacatgac    1380
atagaagccc agtggcatga tgagagccac ctcaacaaat acttcctttt caacaaaccc    1440
actaaaatcc tatctccaga gtattgctgg gactatcaga taggcctgcc ttcagatatt    1500
aaaagtgtca aggtagcttg gcagacaaaa gagtataatt tggttagaaa taatgtctga    1560
cttcaaattg tgatggaaac ttgacactat tactctggct aattcctcaa acaagtagca    1620
acacttgatt tcaactttta aagaaacaa tcaaaaccaa acccactac catggcaaac    1680 agatgatttc tcctgacacc ttgagcctgt aatatgtgag aaagagtcta tggcaagtaa    1740
tcaggtataa attctcaatg atttcttata tattctgggt cttgggaaaa cttgattcta    1800
gaaatcaaaa ttaatttgac aaggaaaag cagatgccgg aaacttcttc ccagtctgtc    1860
atacaattca ccactggcca ggtgctgaga gaagcattag ggaacagtgt gggttgtgtc    1920
agagttggac ggctccatcc ctttggcttc attatcttcc tcctcatgga gattctaaag    1980
caacccagag aggctttgca gccagagacc tttaataagg atgccaatgt gaccatcagt    2040
ctgtaaaagc tgatggctcc aggagcgctg gcagtccagg ccccactagg ctattgtttc    2100
tgtcctgggc ataaggagg cagagagtgc caataggtac tttggtggca catgttcaga    2160
gtccaggaaa aatcaagggt gaccacttag agggacatag gacttggggt tggtgattga    2220
actgagttac aaacacagac agctttcttc aggatgacta cagcaggaa ttgaatggaa    2280 agtgtgttca ttttgttttg cccaaattgt attcatgctg ttagctttgt gtgttgagcc    2340
ctgtggagag ggtgtgactg tatcagggaa ggagagtacc tcagcggact gaggaccagc    2400
accctattat atcagaagac aatctctcat catcaggtcc tacctacaac ctgctctgaa    2460
cctccgagtt cctcagccca tcgtgttcca gtgtggggc ctgtatggag caggtgactg    2520
aagacaaagc cccctgtcac atgacctcat ttcccctgct ctagtactat gcaagtgtga    2580
cagccagcca gccagatgta ctggacaaca taggaaccga ctttatggca atgggagccg    2640
cagtcactac aacggagctg ctgaaggttc tgttccccgc tctgagagcc tgcaggagcc    2700
cctgtatagg tggttctcaa cctatgggtc gcgacccctt tgggaagtgt taaatgaccc    2760
tttcacaggt gtcccctaag acggttaaaa acatagata tttccactct gactggtaac    2820
agtagcagaa ttacagttat gaaatagcaa gggaaataat tctggggttc gtgtcatcca    2880
taccatgagg agctacatta ggtcacatca ttagggaagt tgagaagcat agctctactt    2940
gggtatttaa gcaaattatg caaaggggt tgtcgctctg tgttctgtgt atgcatatat    3000
ttatattttg cttgtcttcc agtttaggtc aatctgtttc ttcctttaag cagtttattt    3060
aaaaggccat tgcaccatct tggtgaacag catgagggg ttcaataaaa aataggatct    3120
tacctttgtc cacagggctc tacctcttac ttttcaattg tgaacaaaaa aggtcgcaca    3180
cccagaggca acaaaaccca cagaattcct gaaccaatgg gagatgccaa tggaagcaga    3240
gcttgcacat ctgctaaaaa ttctgcctct ctgtcactgt gctggatccg tctaaagtgg    3300
gacagttcaa tggtctgaaa gtttcaaaaa ggctggggaa tttgagggga ttttttttta    3360
aaataaaatt gatccaagtt taaatctcta atgagtaagc ttaggatttt attaaaggta    3420
atttttagac attcttcaaa ataagaattc                                     3450
```

<210> SEQ ID NO 2
<211> LENGTH: 371
<212> TYPE: PRT
<213> ORGANISM: Mus musculus

```
<400> SEQUENCE: 2

Met Asn Val Lys Gly Lys Val Ile Leu Leu Met Leu Ile Val Ser Thr
1               5                   10                  15

Val Val Val Val Phe Trp Glu Tyr Val Asn Ser Pro Asp Gly Ser Phe
                20                  25                  30

Leu Trp Ile Tyr His Thr Lys Ile Pro Glu Val Gly Glu Asn Arg Trp
            35                  40                  45

Gln Lys Asp Trp Trp Phe Pro Ser Trp Phe Lys Asn Gly Thr His Ser
        50                  55                  60

Tyr Gln Glu Asp Asn Val Glu Gly Arg Arg Glu Lys Gly Arg Asn Gly
65                  70                  75                  80

Asp Arg Ile Glu Glu Pro Gln Leu Trp Asp Trp Phe Asn Pro Lys Asn
                85                  90                  95

Arg Pro Asp Val Leu Thr Val Thr Pro Trp Lys Ala Pro Ile Val Trp
                100                 105                 110

Glu Gly Thr Tyr Asp Thr Ala Leu Leu Glu Lys Tyr Tyr Ala Thr Gln
            115                 120                 125

Lys Leu Thr Val Gly Leu Thr Val Phe Ala Val Gly Lys Tyr Ile Glu
        130                 135                 140

His Tyr Leu Glu Asp Phe Leu Glu Ser Ala Asp Met Tyr Phe Met Val
145                 150                 155                 160

Gly His Arg Val Ile Phe Tyr Val Met Ile Asp Asp Thr Ser Arg Met
                165                 170                 175

Pro Val Val His Leu Asn Pro Leu His Ser Leu Gln Val Phe Glu Ile
                180                 185                 190

Arg Ser Glu Lys Arg Trp Gln Asp Ile Ser Met Met Arg Met Lys Thr
            195                 200                 205

Ile Gly Glu His Ile Leu Ala His Ile Gln His Glu Val Asp Phe Leu
        210                 215                 220

Phe Cys Met Asp Val Asp Gln Val Phe Gln Asp Asn Phe Gly Val Glu
225                 230                 235                 240

Thr Leu Gly Gln Leu Val Ala Gln Leu Gln Ala Trp Trp Tyr Lys Ala
                245                 250                 255

Ser Pro Glu Lys Phe Thr Tyr Glu Arg Arg Glu Leu Ser Ala Ala Tyr
            260                 265                 270

Ile Pro Phe Gly Glu Gly Asp Phe Tyr Tyr His Ala Ala Ile Phe Gly
        275                 280                 285

Gly Thr Pro Thr His Ile Leu Asn Leu Thr Arg Glu Cys Phe Lys Gly
290                 295                 300

Ile Leu Gln Asp Lys Lys His Asp Ile Glu Ala Gln Trp His Asp Glu
305                 310                 315                 320

Ser His Leu Asn Lys Tyr Phe Leu Phe Asn Lys Pro Thr Lys Ile Leu
                325                 330                 335

Ser Pro Glu Tyr Cys Trp Asp Tyr Gln Ile Gly Leu Pro Ser Asp Ile
            340                 345                 350

Lys Ser Val Lys Val Ala Trp Gln Thr Lys Glu Tyr Asn Leu Val Arg
        355                 360                 365

Asn Asn Val
    370

<210> SEQ ID NO 3
<211> LENGTH: 36
<212> TYPE: DNA
<213> ORGANISM: Mus musculus
```

```
<400> SEQUENCE: 3
acaaaagctt gacatggatg tcaagggaaa agtaat                                    36

<210> SEQ ID NO 4
<211> LENGTH: 28
<212> TYPE: DNA
<213> ORGANISM: Mus musculus

<400> SEQUENCE: 4
aattatcgat tcagacatta tttctaac                                             28
```